United States Patent [19]

Ozawa

[11] Patent Number: 4,971,064

[45] Date of Patent: Nov. 20, 1990

[54] ELECTRONIC CLINICAL SPHYGMOMANOMETER

[75] Inventor: Hitoshi Ozawa, Fuji, Japan

[73] Assignee: Terumo Corporation, Tokyo, Japan

[21] Appl. No.: 375,921

[22] Filed: Jul. 6, 1989

[30] Foreign Application Priority Data

Jul. 7, 1988 [JP] Japan .................................. 63-167837

[51] Int. Cl.⁵ .......................................... A61B 5/0225
[52] U.S. Cl. ..................................... 128/681; 128/680
[58] Field of Search .......................... 128/672, 677–686

[56] References Cited

U.S. PATENT DOCUMENTS

| | | | |
|---|---|---|---|
| 4,214,589 | 7/1980 | Sakamoto et al. | 128/680 |
| 4,261,368 | 4/1981 | Danna et al. | |
| 4,459,991 | 7/1984 | Hatschek | 128/681 |
| 4,475,557 | 10/1984 | Hatschek et al. | 128/680 X |
| 4,549,549 | 10/1985 | Furukawa | 128/677 X |
| 4,840,181 | 6/1989 | Yamaguchi | 128/680 |

FOREIGN PATENT DOCUMENTS 0053228 6/1982 European Pat. Off. .
0154995 9/1985 European Pat. Off. .
2165052A 4/1986 United Kingdom .

OTHER PUBLICATIONS

European Search Report Conducted by Examiner B. W. Hunt, Completed on Oct. 11, 1989, in the Hague (4 prior art references cited).

Primary Examiner—Angela D. Sykes
Attorney, Agent, or Firm—Staas & Halsey

[57] ABSTRACT

In an electronic clinical sphygmomamometer of the type which measures blood pressure on the basis of a Korotkoff-sound signal in a pulse-wave gate signal, the level of a detected pulse-wave signal is compared with a predetermined threshold level to form a pulse-wave gate signal the duration of which corresponds to a period over which the level of the pulse-wave signal is higher than the predetermined threshold level. If no Korotkoff-sound detection signal is provided in the pulse-wave gate signal thus formed, the duration of the pulse-wave gate signal is extended by a predetermined time period. The thus-extended duration of the pulse-wave period required to measure the systatic blood pressure gate signal serves as the measurement.

9 Claims, 5 Drawing Sheets

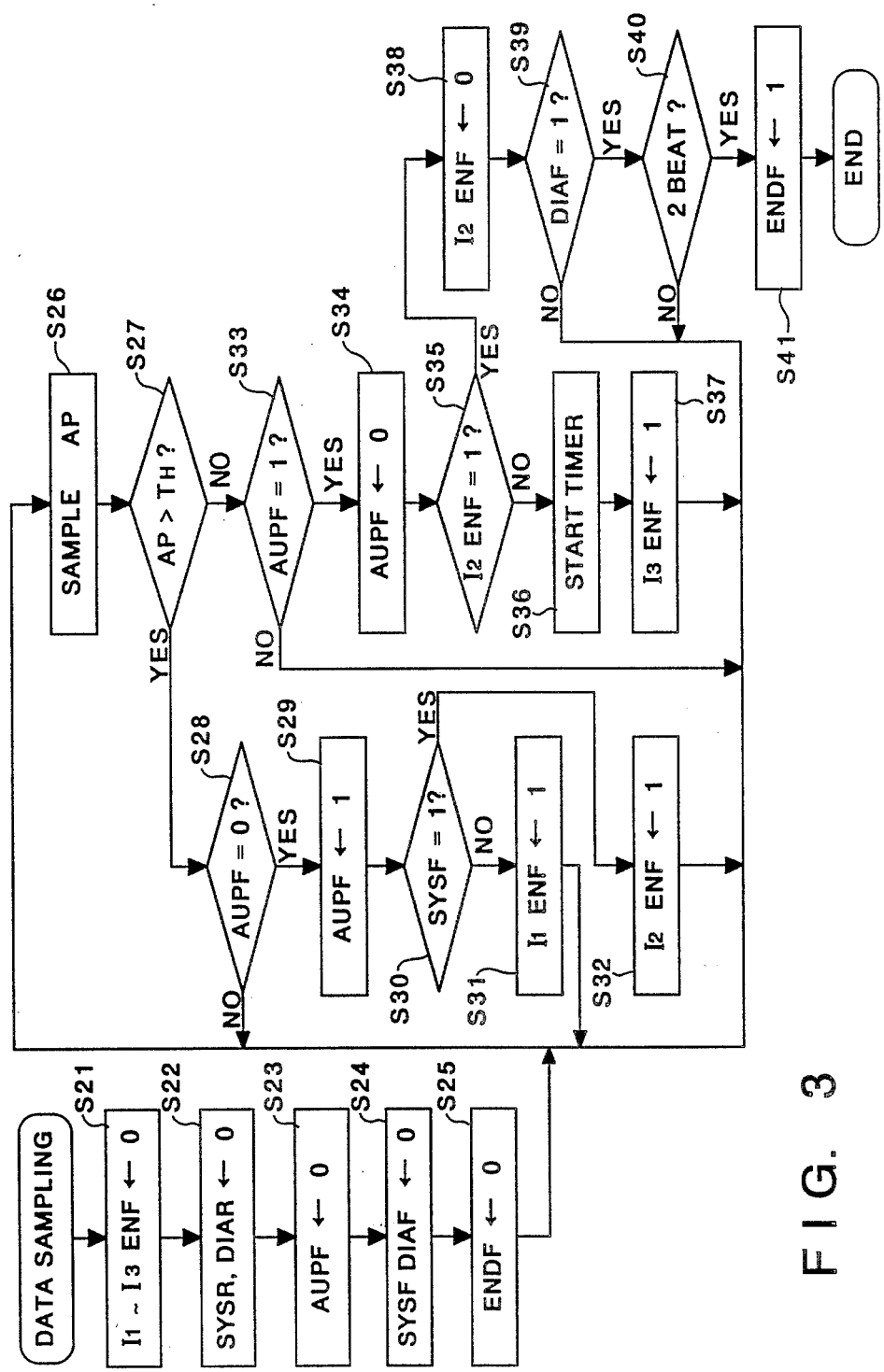
F I G. 3

ELECTRONIC CLINICAL SPHYGMOMANOMETER

BACKGROUND OF THE INVENTION

The present invention relates generally to an electronic clinical sphygmomanometer and, more particularly, to an electronic clinical sphygmomanometer for measuring blood pressure on the basis of a Korotkoff-sound signal in a pulse-wave gate signal.

In general, conventional clinical sphygmomanometers of this type are susceptible to external noise derived from such factors as motion of the body since Korotkoff-sound signals are weak, thus occasionally resulting in erroneous measurements. To eliminate such erroneous measurements, Japanese Patent Application No. 279225/1986 proposes an electronic clinical sphygmomanometer of the type which is arranged to utilize the correlation between a pulse-wave signal and a Korotkoff-sound signal to compare the level of the pulse-wave signal with a predetermined level, thereby creating a pulse-wave gate signal for the purpose of improving noise resistance.

However, the wave forms of pulse-wave signals are not constant and, in addition, the correlation between pulse-wave signals and Korotkoff-sound signals is not constant. As a result, a Korotkoff-sound signal occasionally deviates from a pulse-wave gate, and it has therefore been difficult to reliably detect Korotkoff-sound signals.

SUMMARY OF THE INVENTION

To eliminate the above-described problems with the prior art, it is a primary object of the present invention to provide an electronic clinical sphygmomanometer which is capable of effecting highly reliable measurement of blood pressure by forming an appropriate pulse-wave gate.

According to the present invention the foregoing objects are attained by providing an electronic clinical sphygmomanometer comprising a Korotkoff-sound signal detecting means for detecting a Korotkoff-sound signal and outputting a predetermined Korotkoff-sound detection signal, a pulse-wave signal detecting means for detecting a pulse-wave signal, a pulse-wave gate signal generating means for generating a pulse-wave gate signal the duration of which corresponds to at least the period during which the level of the pulse-wave signal is higher than a predetermined threshold level by comparing the pulse-wave signal detected by the pulse-wave signal detecting means with the predetermined threshold level, and an extending means for extending the duration of the pulse-wave gate signal by a predetermined time period when the aforesaid Korotkoff-sound detection signal is not provided in the pulse-wave gate signal generated by the pulse-wave gate signal generating means.

In a preferred embodiment, the extending means is arranged to serve during at least a measurement period allocated for the measurement of the systolic blood pressure.

In a preferred embodiment, the Korotkoff-sound signal detecting means comprises a first filter circuit which efficiently passes a Korotkoff-sound signal component at a pressure close to the systolic blood pressure, a first single-shot circuit arranged to be triggered by the leading edge of a signal output from the first filter circuit to thereby output a Korotkoff-sound detection signal, a second filter circuit which efficiently passes a Korotkoff-sound signal component at a pressure close to the diastolic blood pressure, and a second single-shot circuit arranged to be triggered by the trailing edge of a signal output from the second filter circuit to thereby output a Korotkoff-sound detection signal.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 3 is a flow chart of the data sampling executed in the embodiment;

DESCRIPTION OF THE PREFERRED EMBODIMENT

An embodiment of the present invention will be described in detail below with reference to the accompanying drawings.

Figure 1:
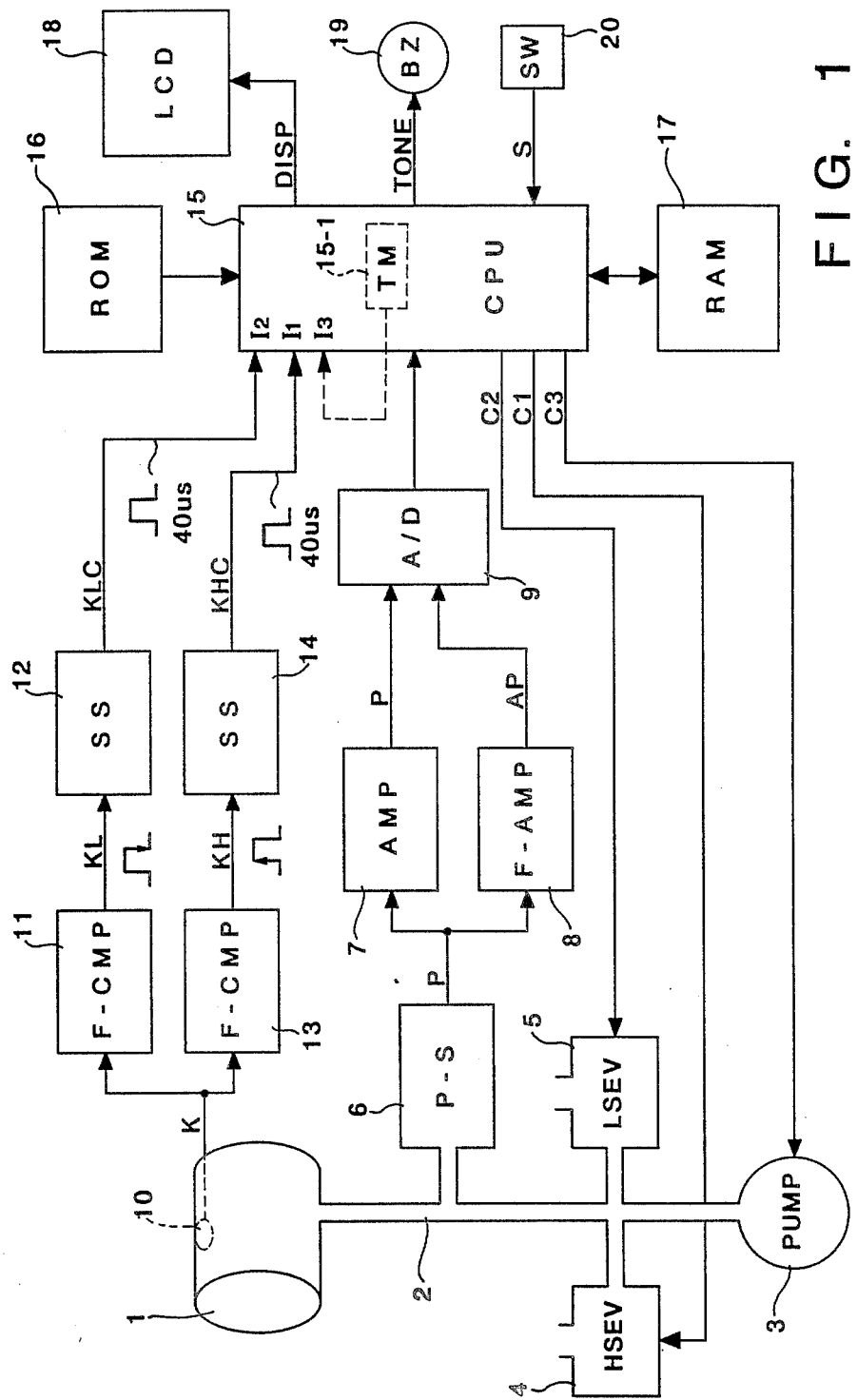
FIG. 1 is a block diagram showing an embodiment of an electronic clinical sphygmomanometer according to the present invention.
Figure 2:
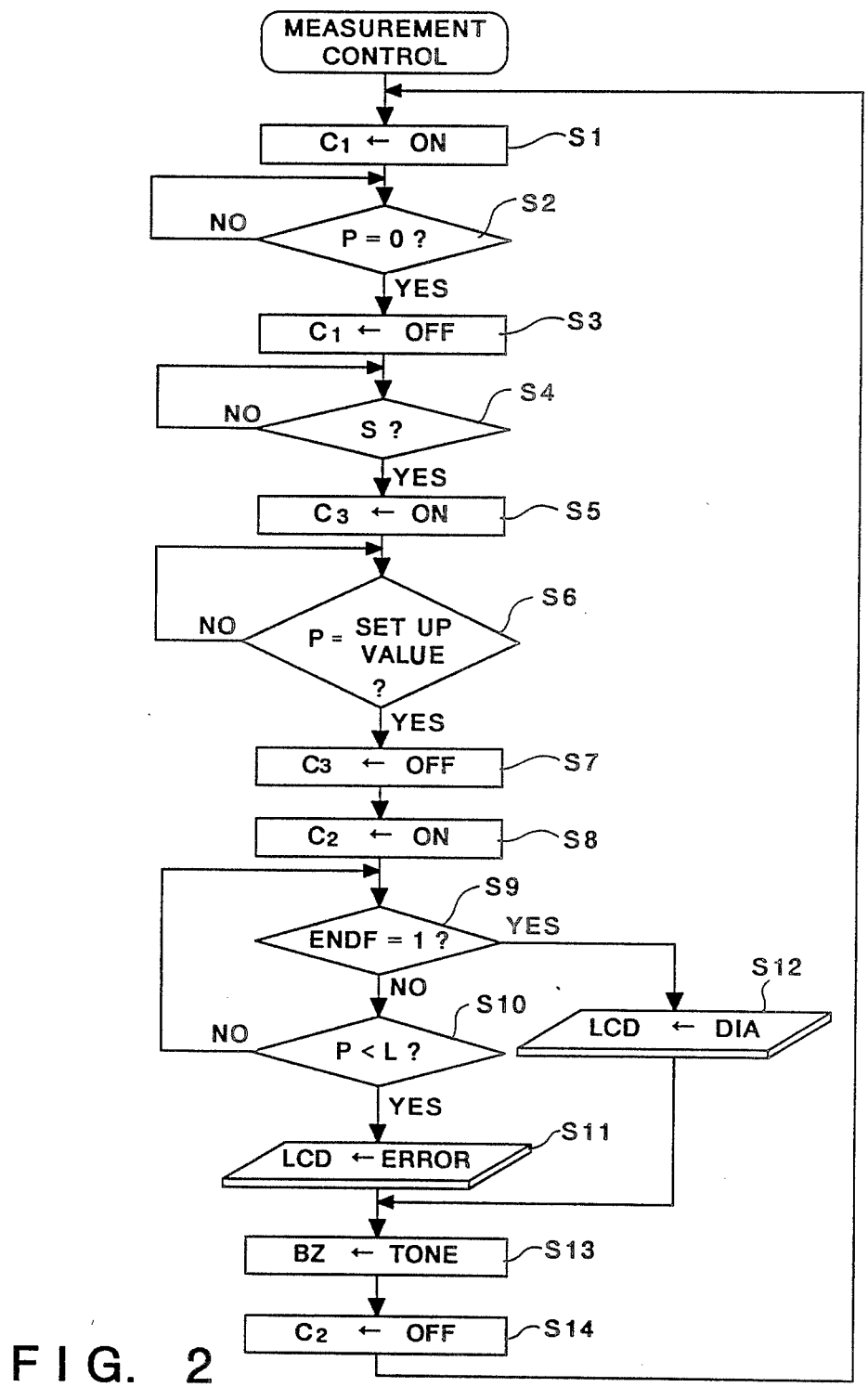
FIG. 2 is a flow chart of control provided over the measurement of blood pressure in the embodiment.
Figure 4:
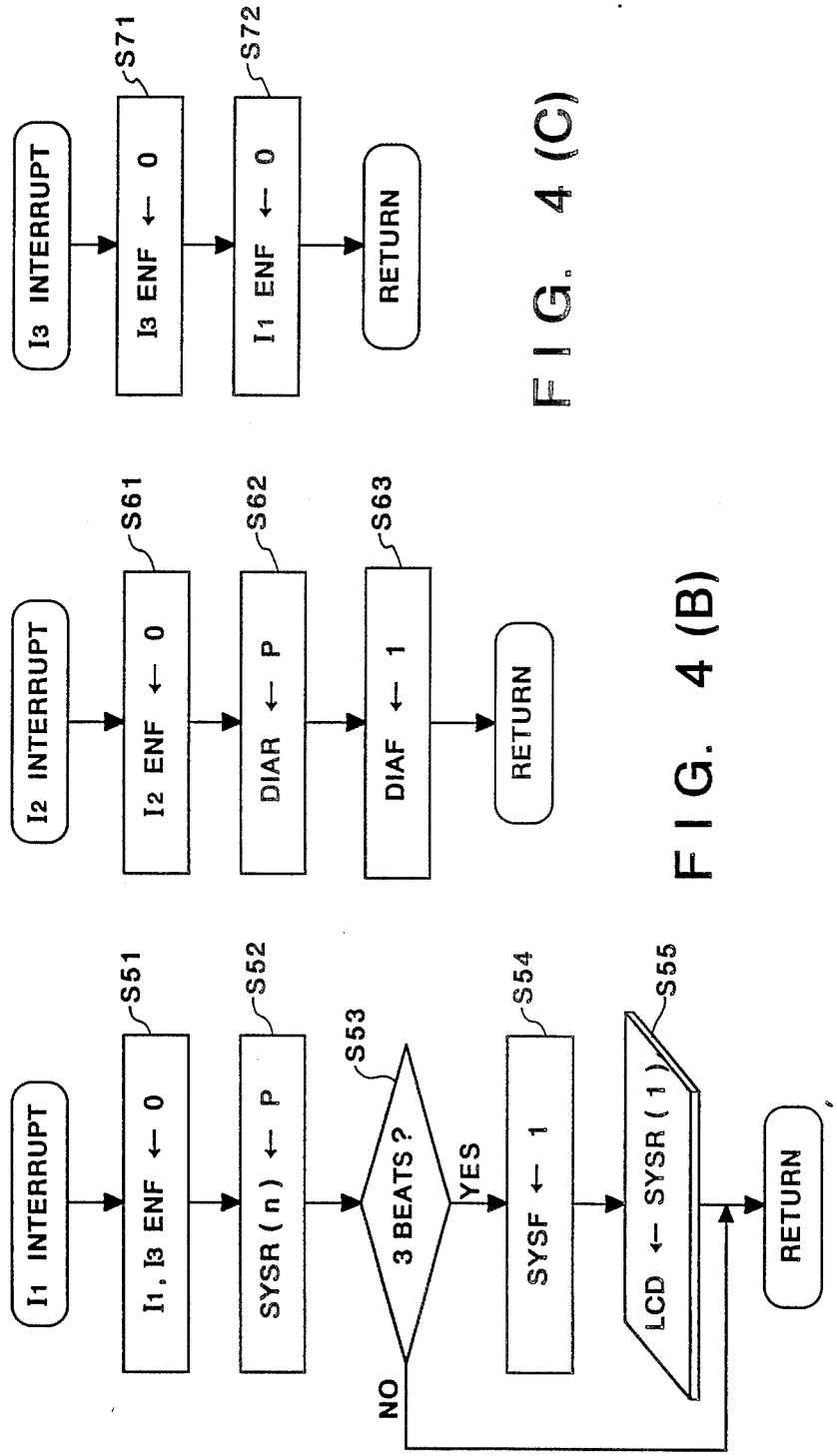
FIGS. 4(A) to 4(C) are flow charts which show interruption routines $I_1$, $I_2$, and $I_3$, respectively.

FIG. 1 is a block diagram showing an embodiment of an electronic clinical sphygmomanometer according to the present invention. In the figure, a cuff, denoted by 1, is adapted to be wound around the upper arm of a person so as to constrict the artery. A rubber tube, denoted by 2, constitutes an inlet/outlet passage through which pressurized air is fed to, and discharged from, the cuff 1. A pump, denoted by 3, serves to feed pressurized air into the cuff 1. A high-speed exhaust valve (HSEV), denoted by 4, serves to exhaust air from the cuff 1 at high speed. A slow-speed exhaust valve (LSEV), denoted by 5, serves to decrease the pressure in the cuff 1 at a constant rate (for example, 2-3 mmHg/second). A pressure sensor (P-S), denoted by 6, serves to detect the pressure in the cuff 1 and output a cuff-pressure signal P. An amplifier (AMP), denoted by 7, serves to amplify the cuff-pressure signal P. A filter amplifier (F-AMP), denoted by 8, serves to extract a pulse-wave signal component AP from the cuff-pressure signal P and amplify the extracted signal component. An A/D converter (A/D) is denoted by 9, and this serves to convert either the cuff-pressure signal P or the pulse-wave signal AP into digital data. A microphone, denoted by 10, serves to pick up a Korotkoff-sound signal K. A filter comparator (F-CMP) 11 is arranged to efficiently pass a Korotkoff-sound signal at a pressure close to the diastolic blood pressure (for example, a signal component which ranges from 10 Hz to 80 Hz), to compare the Korotkoff-sound signal with a predetermined threshold value and to output a pulse signal KL representing the result of this comparison. A single-shot circuit (SS), denoted by 12, is arranged to output a pulse signal KLC of fixed pulse width (e.g., 40 μs) in response to the trailing edge of the KL signal. A filter comparator (F-CMP) is denoted by 13, and this is arranged to efficiently pass a Korotkoff-sound signal at a pressure close to the systolic blood pressure (for example, a signal component which ranges from 10 Hz to 60 Hz), to compare the Korotkoff-sound signal with a predetermined threshold value and to output a pulse signal KH representing the result of this comparison. A single-shot circuit (SS), denoted by 14, is arranged to output a pulse signal KHC of fixed pulse width (e.g., 40 μs) in response to the leading edge of the KH signal. A central processing unit (CPU), denoted by 15, is arranged to execute the main control of the electronic clinical sphygmomanometer. The CPU 15 is provided with interruption inputs $I_1$, $I_2$ and $I_3$. A ROM is denoted by 16 and a control program to be executed by the CPU 15, for example, a control program such as that shown in FIGS. 2, 3 and 4 is stored in the ROM 16. A RAM is denoted by 17, and is used as a work area by the CPU 15. A timer (TM) is denoted by 15-1, and is arranged to measure the duration of a predetermined time period (for example, 60 ms) until it reaches a time-out state. A liquid-crystal display (LCD), denoted by 18, serves to display the systolic blood pressure (SYS), the diastolic blood pressure (DIA), error information and so on. A buzzer (BZ), denoted by 19, serves to inform a user of, for example, the completion of measurement. A measurement start switch (SW) is denoted by 20, and the user can actuate the switch 20 to command the sphygmomanometer to start a measurement operation.

FIG. 2 is a flow chart of the control provided over the measurement of blood pressure in the embodiment. When electrical power is supplied to the present apparatus, this control process is started. In Step S1, the high-speed exhaust valve 4 is opened and, in Step S2, the process waits for the cuff pressure P to reach zero. When the cuff pressure P reaches zero, the high-speed exhaust valve 4 is closed in Step S3. In Step S4, the process waits for the measurement start switch (SW) 20 to be pressed. When the switch (SW) 20 is pressed, driving of the pump 3 is started in Step S5. In Step S6, the process waits for the cuff pressure P to reach a set value (for example, 140 to 150 mmHg). When the cuff pressure P reaches the set value, the driving of the pump 3 is stopped in Step S7. In Step S8, the slow-speed exhaust valve 5 is opened. In this manner, the cuff pressure P is made to decrease at a constant rate (2-3 mmHg/second) and, during this time, the data sampling shown in FIGS. 3 and 4(A) to 4(C) is executed. In Step S9, it is determined whether an end-of-measurement flag ENDF is set to "1". After the systolic blood pressure SYS and the diastolic blood pressure DIA have been measured, the end-of-measurement flag ENDF is set to "1". If the end-of-measurement flag ENDF is set to "1", this indicates that the end of the measurement is normal. Then, the process proceeds to Step S12, where the diastolic blood pressure is displayed on the LCD 18. Incidentally, the systolic blood pressure SYS is displayed at a previous time. If the end-of-measurement flag ENDF is not set to "1", the process proceeds to Step S10, where it is determined whether or not the cuff pressure P is lower than a predetermined low pressure L (for example, 20 mmHg). If the cuff pressure P is not lower than the predetermined pressure L, it is determined that the cuff pressure P is within a measurable range, and the flow returns to Step S9. If the cuff pressure P is lower than the predetermined pressure L, it is determined that the cuff pressure P has fallen below the measurable range, and the process proceeds to Step S11. In Step S11, the characters "ERROR" are displayed on the LCD 18. In Step S13, the CPU 15 transmits a tone signal TONE to the buzzer 19. The tone signal TONE transmitted for the case of a normal end differs from that transmitted for the case of an abnormal end. In Step S14, the slow-speed exhaust valve 5 is closed, and the process returns to Step S1. In Steps S1 to S3, the air remaining in the cuff 1 is exhausted at high speed and, in Step S4, the process waits for the next measurement to be started.

FIG. 3 is a flow chart of data sampling executed in the embodiment. This process is started after Step S8 of FIG. 2 has been executed. In Steps S21 to S25, a sequence of initialization steps is executed. More specifically, in Step S21, interruption-enable flags $I_1$ to $I_3$ (ENF) for the respective interruption routines $I_1$, $I_2$, and $I_3$ are all reset to an interruption-unable state (0). In Step S22, the contents of both a systolic-blood-pressure register SYSR and a diastolic-blood-pressure register DIAR are cleared. In Step S23, a pulse-wave flag AUPF is cleared which indicates whether the level of the pulse-wave signal AP exceeds a return-line level $T_H$. In Step S24, the end-of-systolic-measurement flag SYSF and the detection-of-diastolic flag DIAF are cleared. In Step S25, the end-of-measurement flag ENDF is cleared.

In Step S26, the pulse-wave signal AP is sampled. In Step S27, it is determined whether the pulse-wave signal AP is higher than the return-line level $T_H$. For example, if the pulse-wave signal AP provided at the input of the A/D converter 9 ranges between 0 and 3 volts, the return-line level $T_H$ could be set at 1 volt.

If the level of the pulse-wave signal AP is higher than the return-line level $T_H$, it is determined in Step S28 whether or not the value of the pulse-wave flag AUPF is "0". If it is determined, in Step S28, that the pulse-wave flag AUPF has the value 0, this indicates that the level of the pulse-wave signal AP has exceeded the return-line level $T_H$. The process then proceeds to Step S29, in which "1" is set in the pulse-wave flag AUPF. In Step S30, it is determined whether or not the value of an end-of-systolic-measurement flag SYSF is "1". If the value of the end-of-systolic-measurement flag SYSF is not "1", this indicates that the systolic blood pressure is being measured. Therefore, in Step S31, "1" is set in the interruption-enable flag $I_1$ENF so that interruption based on the signal KHC is enabled. The time interval which elapses until this flag $I_1$ENF is reset from "1" to "0" corresponds to the duration of a pulse-wave gate signal used for determining the systolic blood pressure. If it is determined, in Step S30, that the value of the end-of-systolic-measurement flag SYSF is "1", this indicates that the diastolic blood pressure is being measured. Therefore, in Step S32, "1" is set in the interruption-enable flag $I_2$ENF so that interruption based on the signal KLC is enabled. The time interval which elapses until this flag $I_2$ENF is reset from "1" to "0" corresponds to the duration of a pulse-wave gate signal used for determining the diastolic blood pressure. If it is determined, in Step S28, that the value of the pulse-wave flag AUPF is not "0", this indicates that the level of the pulse-wave signal AP already exceeds the return-line level $T_H$. The process then merely continues the sampling of the pulse-wave signal AP, waiting for the interruption routine $I_1$ or $I_2$ to be executed.

If it is determined, in Step S27, that the level of the pulse-wave signal AP is not higher than the return-line level $T_H$, it is determined in Step S33 whether or not the value of the pulse-wave flag AUPF is "1". If it is determined that the pulse-wave flag AUPF has the value 1, this indicates that the level of the pulse-wave signal AP has dropped below the return-line level $T_H$. The process proceeds to Step S34, in which "0" is set in the pulse-wave flag AUPF. In Step S35, it is determined whether or not the value of the interruption-enable flag $I_2$ENF is "1". If the value of the interruption-enable flag $I_2$ENF is not "1", this indicates that the level of the pulse-wave signal AP has dropped below the return-line level $T_H$ when the value of the interruption-enable flag $I_1$ENF is "1". This fact means that a signal KHC has not yet been generated during the period in which the value of the interruption-enable flag $I_1$ENF is "1". The flow then proceeds to Step S36, where the timer 15-1 (for measuring, e.g., 60 ms) is started to extend the duration of a pulse-wave gate signal used for determining the systolic blood pressure. In Step S37, "1" is set in the timer-interruption-enable flag $I_3$ENF so that timer interruption is enabled.

If it is determined, in Step S35, that the value of the interruption-enable flag $I_2$ENF is "1", as in the case of the interruption-enable flag $I_1$ENF mentioned above, it means that the signal KLC has not been generated during the period in which the value of the interruption-enable flag $I_2$ENF is "1". In this embodiment, in such a case, the duration of the pulse-wave gate signal is not extended, and the process proceeds to Step S38, where "0" is set in the interruption-enable flag $I_2$ENF. In Step S39, it is determined whether the value of the detection-of-diastolic flag DIAF is "1". If the value of the detection-of-diastolic flag DIAF is not "1", this means that no signal KLC has been sampled within the duration of the pulse-wave gate. Therefore, the process returns to Step S26. If the value of the detection-of-diastolic flag DIAF is "1", this means that at least one signal KLC has been sampled within the duration of the pulse-wave gate signal used for determining the diastolic blood pressure. The process, therefore, proceeds to Step S40, where it is determined whether the state of no signal KLC being generated continues subsequently over a period corresponding to two beats during the period in which the interruption-enable flag $I_2$ENF is "1". If such a state does not occur during the period corresponding to two beats, the process returns to Step S26. If this state occurs during such a period, it means that the end of the data sampling is normal. Then, the process proceeds to Step S41, where "1" is set in the end-of-measurement flag ENDF.

If it is determined, in Step S33, that the value of the pulse-wave flag AUPF is not "1", this indicates that the level of the pulse-wave signal AP has already fallen below the return-line level $T_H$, and the process merely continues the sampling of the pulse-wave signal AP, waiting for the level of the pulse-wave signal AP to exceed the return-line level $T_H$.

FIGS. 4(A) to 4(C) are flow charts of the interruption routines $I_1$, $I_2$, and $I_3$, respectively.

If a signal KHC is generated during the period in which the value of the interruption-enable flag $I_1$ENF is "1", the process enters the interruption routine $I_1$ shown in FIG. 4(A). In Step S51, "0" is set in the interruption-enable flag $I_1$ENF in order to prevent the interruption $I_1$ from occurring repeatedly. Since the value of the interruption-enable flag $I_3$ENF may be "1" at this point in time, "0" is also set in the interruption-enable flag $I_3$ENF. In Step S52, the cuff pressure P at the time of generation of the signal KHC is sampled, and data on the cuff-pressure P are stored in systolic-blood-pressure registers SYSR(n: n=1, 2, 3). The first data is stored in the register SYSR(1). Subsequently, the second and third data are likewise stored in the registers SYSR(2) and (3), respectively, so that the data corresponding to pulse waves for three beats are stored. In Step S53, it is determined whether or not the data on the cuff pressures P for three pulse-wave beats have been stored. If it is determined that the data for three beats have not yet been stored, the process returns. If the data for three beats have been stored, this means that the data required to confirm the systolic blood pressure has been sampled. Accordingly, in Step S54, "1" is set in the end-of-systolic-measurement flag SYSF and, in Step S55, the data which represents the blood pressure corresponding to the first beat is read from the systolic-blood-pressure register SYSR(1) and is in turn displayed on the LCD 18 as the systolic blood pressure SYS.

If a signal KLC is generated during the period in which the value of the interruption-enable flag $I_2$ENF is "1", the process enters the interruption routine $I_2$ shown in FIG. 4(B). In Step S61, "0" is set in the interruption-enable flag $I_2$ENF in order to prevent the interruption $I_2$ from occurring repeatedly. In Step S62, the cuff pressure P at the time of generation of the signal KLC is sampled, and data on the cuff-pressure P is stored in the diastolic-blood-pressure register DIAR. In this manner, the contents of the diastolic-presssure register DIAR are rewritten with new sampled data. Since data has been detected which may represent the diastolic blood pressure, in Step S63, "1" is set in the end of diastolic-blood-pressure measurement flag DIAF.

If a time-out signal is generated during the period in which the value of the interruption-enable flag $I_3$ENF is "1", the process enters the interuption routine $I_3$ shown in FIG. 4(C). In Step S71, "0" is set in the interruption-enable flag $I_3$ENF. In Step S72, "0" is also set in the interruption-enable flag $I_1$ENF since the timer 15-1 has reached the time-out state (since 60 ms have elapsed), thereby closing the pulse-wave gate.

Figure 5:
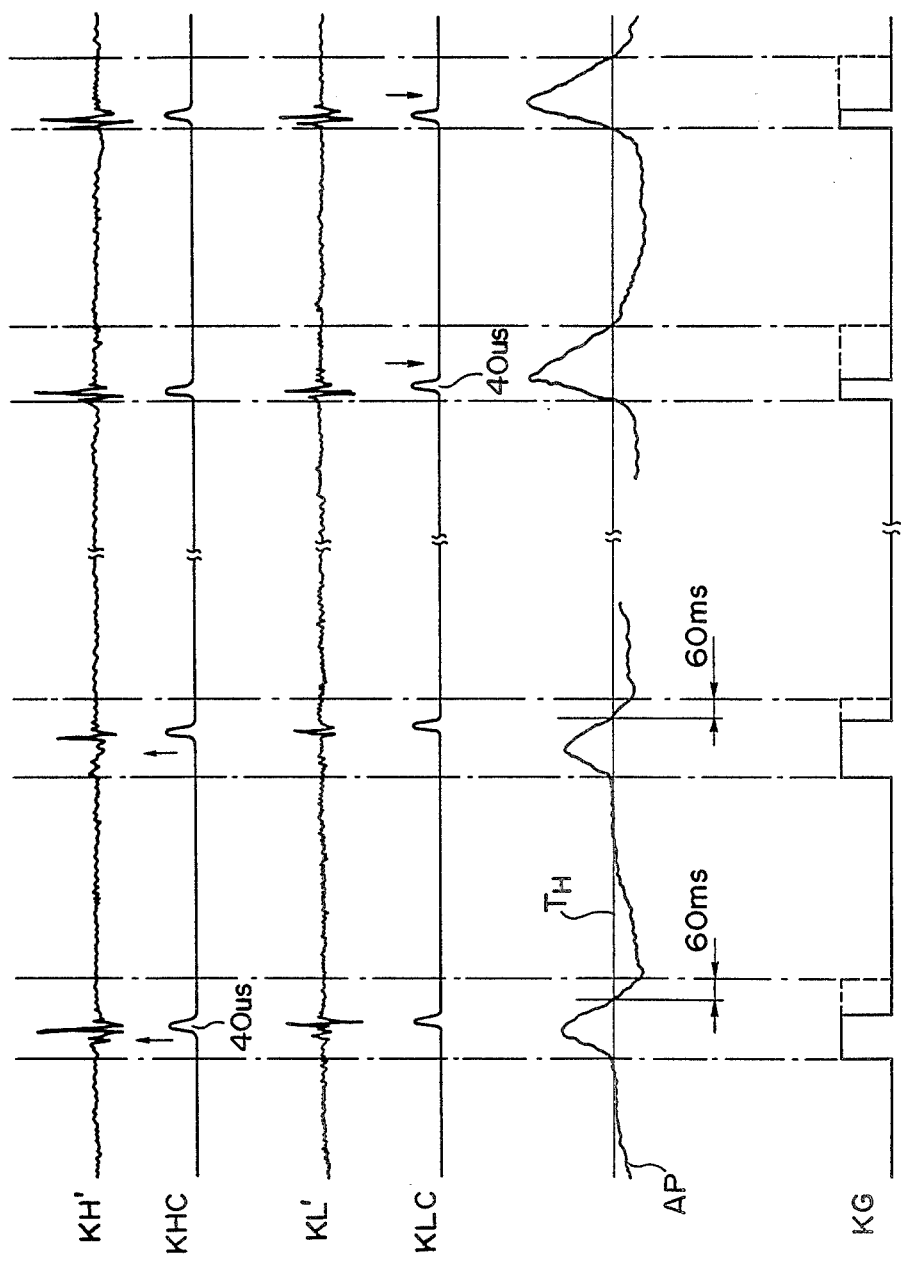
FIG. 5 is a timing chart of the data sampling executed in the embodiment.

FIG. 5 is a timing chart of the data sampling executed in the embodiment. In the figure, a signal KH' is a signal which has passed through the filter comparator (F-CMP) 13, and a signal KL' is a signal which has passed through the filter comparator (F-CMP) 11. The left half of FIG. 5 shows the states of respective signals during the period of measurement of the systolic blood pressure (the value of the flag SYSF="0"). As shown in this left half, a pulse-wave gate signal KG (the value of the flag $I_1$ENF="1") is reset if the signal KHC is generated during the duration of the pulse-wave gate signal KH. If no signal KHC is generated while KG is high, the duration of the pulse-wave gate signal KG is extended by 60 ms from the moment that the level of the pulse-wave signal AP falls below the return-line level $T_H$. This extension is provided in order to accommodate the phase relationship between the Korotkoff-sound signal KHC and the pusle-wave signal AP corresponding to a pressure close to the systolic blood pressure.

The right half of FIG. 5 shows the states of the respective signals during the period of measurement of the diastolic blood pressure (the value of the flag SYSF="1"). As shown in this right half, the pulse-wave gate signal KG (the value of the flag $I_2$ENF="1") is reset if the signal KLC is generated during the duration of the pulse-wave gate signal KG. If no signal KLC is generated while KG is high, the pulse-wave gate signal KG is reset at the time that the level of the pulse-wave signal AP falls below the return-line level $T_H$. This setting is likewise intended to accommodate the phase relationship between the Korotkoff-sound signal KLC and the pulse-wave signal AP corresponding to a pressure close to the diastolic blood pressure.

Although in the above-described embodiment the pulse-wave signal AP is separated and extracted from the detected cuff-pressure signal P, the method of picking up the pulse-wave signal AP is not limited to the above-described one. As another example, a microphone may be used to pick up a heart-beat signal and this heart-beat signal may be used as the pulse-wave signal AP.

The above embodiment is explained with reference to the example in which the systolic blood pressure SYS and the diastolic blood pressure DIA are measured during the step of decreasing the cuff pressure while exhausting air from the cuff 1 at slow speeds, but this example is not construed as a limiting one. As another example, the diastolic blood pressure DIA and the systolic blood pressure SYS may be measured during the step of increasing the cuff pressure at a fixed speed. In this case, the pressure measured when a Korotkoff-sound signal first appears corresponds to the diastolic blood pressure DIA, while the pressure measured when the Korotkoff-sound signal disappears corresponds to the systolic blood pressure SYS.

As described above, in accordance with the present invention, since a pulse-wave gate is always accurately opened with respect to the duration of a Korotkoff-sound signal, it is possible to effect highly reliable measurement of blood pressure.

As many apparently widely different embodiments of the present invention can be made without departing from the spirit and scope thereof, it is to be understood that the invention is not limited to the specific embodiments thereof except as defined in the appended claims.

What is claimed is:

1. An electronic clinical sphygmomanometer for measuring blood pressure on the basis of a Korotkoff-sound signal in a pulse-wave gate signal, comprising:
   Korotkoff-sound signal detecting means for detecting a Korotkoff-sound signal and outputting a predetermined Korotkoff-sound detection signal;
   pulse-wave signal detecting means for detecting a pulse-wave signal;
   pulse-wave gate signal generating means for generating a pulse-wave gate signal the duration of which includes a period over which the level of said pulse-wave signal is higher than a predetermined threshold level, by comparing said pulse-wave signal, detected by said pulse-wave signal detecting means, with said predetermined threshold level; and
   extending means for extending the duration of said pulse-wave gate signal by a predetermined time period when said Korotkoff-sound detection signal is not output while said pulse-wave gate signal is generated by said pulse-wave gate signal generating means.

2. An electronic clinical sphygmomanometer according to claim 1, wherein said extending means is arranged to serve during at least a measurement period allocated for measurement of systolic blood pressure.

3. An electronic clinical sphygmomanometer according to claim 1, wherein said Korotkoff-sound signal detecting means comprises:

a first filter circuit which efficiently passes a first Korotkoff-sound signal component at a pressure close to the systolic blood pressure,
a first single-shot circuit arranged to be triggered by the leading edge of the first Korotkoff-sound signal component output from said first filter circuit to thereby output the Korotkoff-sound detection signal,
a second filter circuit which efficiently passes a second Korotkoff-sound signal component at a pressure close to diastolic blood pressure, and
a second single-shot circuit arranged to be triggered by the trailing edge of the second Korotkoff-sound signal component output from said second filter circuit to thereby output the Korotkoff-sound detection signal.

4. An electronic clinical sphygmomanometer, comprising:
   Korotkoff-sound signal detection means for outputting a Korotkoff-sound detection signal upon detection of a Korotkoff-sound signal;
   pulse-wave signal detection means for detecting a pulse-wave signal;
   pulse-wave gate signal generation means for generating a pulse-wave gate signal having a duration at least as long as a period over which the pulse-wave signal has a level higher than a predetermined threshold level; and
   extension means for extending the duration of the pulse-wave gate signal by a predetermined time period if the Korotkoff-sound detection signal is not output while the level of the pulse-wave signal is above the predetermined threshold level.

5. An electronic clinical sphygmomanometer according to claim 4, wherein said electronic clinical sphygmomanometer measures systolic and diastolic blood pressures, first measuring one and then measuring the other, and
   wherein said extension means is activated only during measurement of the first of the systolic and diastolic blood pressures.

6. An electronic clinical sphygmomanometer according to claim 5, wherein said Korotkoff-sound signal detection means comprises:
   systolic signal generation means for outputting the Korotkoff-sound detection signal when the Korotkoff-sound signal is detected at a first pressure close to the systolic blood pressure; and
   diastolic signal generation means for outputting the Korotkoff-sound detection signal at a second pressure close to the diastolic blood pressure.

7. A method for measuring blood pressure using an electronic clinical sphygmomanometer, comprising the steps of:
   (a) outputting a Korotkoff-sound detection signal upon detection of a Korotkoff-sound signal;
   (b) detecting a pulse-wave signal;
   (c) generating a pulse-wave gate signal having a duration at least as long as a period over which the pulse-wave signal has a level higher than a predetermined threshold level; and
   (d) extending the duration of the pulse-wave gate signal by a predetermined time period if the Korotkoff-sound detection signal is not output while the level of the pulse-wave signal is above the predetermined threshold level.

8. A method according to claim 7, wherein the blood pressure of a patient is measured by the electronic clinical sphygmomanometer, and wherein said method further comprises the steps of:

(e) varying pressure applied to the patient during a measurement period;

(f) enabling a first interrupt when the pulse-wave gate signal is first generated during the measurement period;

(g) performing the following substeps when the Korotkoff-sound detection signal is output and the first interrupt is enabled:

(g1) storing the pressure applied to the patient;

(g2) disabling the first interrupt; and (g3) setting a first measurement flag indicating that the first one of the systolic and diastolic blood pressure has been measured;

(h) enabling a second interrupt when the first measurement flag is set and the pulse-wave signal is above the predetermined threshold level; and (i) storing the pressure applied to the patient in step (e) as the second of the systolic and diastolic blood pressures when the second interrupt is enabled and the Korotkoff-sound detection signal is output, and wherein said extending in step (d) comprises the step of maintaining enablement of the first interrupt for the predetermined time period beyond a time when the pulse-wave signal falls below the predetermined threshold level.

9. A method according to claim 9, wherein steps (g2) and (g3) are performed after step (g1) has been performed three times for different heartbeats.

* * * * *

UNITED STATES PATENT AND TRADEMARK OFFICE
CERTIFICATE OF CORRECTION

PATENT NO. : 4,971,064

DATED : November 20, 1990

INVENTOR(S) : Ozawa

It is certified that error appears in the above-identified patent and that said Letters Patent is hereby corrected as shown below:

Title PAGE [57] ABSTRACT, line 13, after "wave" insert --gate signal serves as the measurement--;

line 14, after "pressure" insert --.--; delete "gate signal serves as the measurement.".

Signed and Sealed this

Fifth Day of May, 1992

Attest:

DOUGLAS B. COMER

Attesting Officer   Acting Commissioner of Patents and Trademarks